(12) United States Patent
Valentine et al.

(10) Patent No.: US 10,271,844 B2
(45) Date of Patent: Apr. 30, 2019

(54) SURGICAL STAPLING APPARATUS EMPLOYING A PREDICTIVE STAPLING ALGORITHM

(71) Applicant: Covidien LP, Mansfield, MA (US)

(72) Inventors: Kelly Valentine, New Britain, CT (US); Elizabeth Contini, Trumbull, CT (US); Thomas Wingardner, North Haven, CT (US)

(73) Assignee: Covidien LP, Mansfield, MA (US)

( * ) Notice: Subject to any disclaimer, the term of this patent is extended or adjusted under 35 U.S.C. 154(b) by 38 days.

(21) Appl. No.: 15/585,699

(22) Filed: May 3, 2017

(65) Prior Publication Data

US 2017/0333033 A1 Nov. 23, 2017

(51) Int. Cl.
*A61B 17/072* (2006.01)
*A61B 17/068* (2006.01)
*A61B 17/08* (2006.01)
*A61B 90/00* (2016.01)
*A61B 17/00* (2006.01)
(Continued)

(52) U.S. Cl.
CPC ........ *A61B 17/068* (2013.01); *A61B 17/0686* (2013.01); *A61B 17/07207* (2013.01); *A61B 17/08* (2013.01); *A61B 17/115* (2013.01); *A61B 17/1114* (2013.01); *A61B 17/1155* (2013.01); *A61B 2017/00017* (2013.01); *A61B 2017/00022* (2013.01); *A61B 2017/00119* (2013.01); *A61B 2017/00123* (2013.01); *A61B 2017/00398* (2013.01); *A61B 2017/07214* (2013.01);
(Continued)

(58) Field of Classification Search
CPC ................ A61B 17/068; A61B 17/072; A61B 17/07207; A61B 17/115; A61B 17/1155; A61B 17/00234; A61B 2017/00017; A61B 2017/00022; A61B 2017/00398; A61B 2090/032; A61B 2090/064; A61B 2017/07214; A61B 2017/00119; A61B 2017/00123; A61B 2017/00734
USPC .............. 227/19, 175.1, 175.2, 176.1, 180.1; 606/139, 153, 219
See application file for complete search history.

(56) References Cited

U.S. PATENT DOCUMENTS 5,098,405 A 3/1992 Peterson et al.
5,383,880 A 1/1995 Hooven
(Continued)

FOREIGN PATENT DOCUMENTS

CN 101283924 A 10/2008
DE 202006017791 U1 1/2007
(Continued)

OTHER PUBLICATIONS

Japanese Office Action dated Mar. 28, 2018 issued in corresponding Japanese Patent Appln. No. 2017-100787.
(Continued)

*Primary Examiner* — Scott A Smith

(57) ABSTRACT

A surgical device is provided that includes a tool assembly having an anvil assembly and a cartridge assembly configured to grasp tissue therebetween, the cartridge assembly including a plurality of surgical fasteners. A motor is configured to fire one or more surgical fasteners. A sensor determines a first parameter of the tool assembly and a control system adjusts a second parameter of the motor used to fire the one or more surgical fasteners based on the first parameter detected by the sensor.

8 Claims, 10 Drawing Sheets

(51) Int. Cl.
*A61B 17/11* (2006.01)
*A61B 17/115* (2006.01)

(52) U.S. Cl.
CPC ... *A61B 2090/032* (2016.02); *A61B 2090/064* (2016.02); *A61B 2090/0803* (2016.02)

(56) References Cited

U.S. PATENT DOCUMENTS

| | | | |
|---|---|---|---|
| 5,391,153 | A | 2/1995 | Haber et al. |
| 5,535,937 | A | 7/1996 | Boiarski et al. |
| 5,810,811 | A | 9/1998 | Yates et al. |
| 6,533,157 | B1 | 3/2003 | Whitman |
| 6,698,643 | B2 | 3/2004 | Whitman |
| 6,783,524 | B2 * | 8/2004 | Anderson ...... A61B 17/320068 606/1 |
| 6,793,652 | B1 | 9/2004 | Whitman et al. |
| 6,981,941 | B2 | 1/2006 | Whitman et al. |
| 7,023,159 | B2 | 4/2006 | Gorti et al. |
| 7,246,734 | B2 | 7/2007 | Shelton, IV |
| 7,342,983 | B2 | 3/2008 | El-Kik |
| 7,416,101 | B2 | 8/2008 | Shelton, IV et al. |
| 7,464,847 | B2 | 12/2008 | Viola et al. |
| 7,568,603 | B2 | 8/2009 | Shelton, IV et al. |
| 7,717,312 | B2 | 5/2010 | Beetel |
| 7,959,050 | B2 | 6/2011 | Smith et al. |
| 7,963,433 | B2 | 6/2011 | Whitman et al. |
| 8,012,170 | B2 | 9/2011 | Whitman et al. |
| 8,210,413 | B2 | 7/2012 | Whitman et al. |
| 8,479,969 | B2 * | 7/2013 | Shelton, IV ..... A61B 17/00234 227/180.1 |
| 8,499,992 | B2 | 8/2013 | Whitman et al. |
| 8,708,210 | B2 | 4/2014 | Zemlok et al. |
| 8,800,837 | B2 | 8/2014 | Zemlok |
| 9,016,540 | B2 | 4/2015 | Whitman et al. |
| 9,113,877 | B1 | 8/2015 | Whitman et al. |
| 9,204,879 | B2 * | 12/2015 | Shelton, IV ..... A61B 17/07207 |
| 9,364,279 | B2 * | 6/2016 | Houser ............ A61B 17/00234 |
| 9,433,418 | B2 | 9/2016 | Whitman et al. |
| 9,757,128 | B2 * | 9/2017 | Baber .............. A61B 17/07207 |
| 2004/0236347 | A1 | 11/2004 | Karasawa |
| 2012/0116364 | A1 * | 5/2012 | Houser ............ A61B 17/00234 606/1 |
| 2012/0209314 | A1 | 8/2012 | Weir et al. |
| 2012/0211542 | A1 | 8/2012 | Racenet |

FOREIGN PATENT DOCUMENTS

| | | |
|---|---|---|
| DE | 202007006190 U1 | 8/2007 |
| EP | 1980215 A2 | 10/2008 |
| EP | 2027819 A1 | 2/2009 |
| EP | 2047809 A1 | 4/2009 |
| EP | 2245994 A1 | 11/2010 |
| EP | 2777521 A2 | 9/2014 |
| EP | 2789299 A1 | 10/2014 |
| EP | 2898850 A1 | 7/2015 |
| EP | 3064151 A2 | 9/2016 |
| JP | 2007527748 A | 10/2007 |
| JP | 200893437 | 4/2008 |
| JP | 2008259860 A | 10/2008 |
| JP | 200956319 | 3/2009 |
| WO | 2008052791 A1 | 5/2008 |

OTHER PUBLICATIONS

European Office Action for EP 10 250 841.3 dated Sep. 11, 2015.
Extended European Search Report corresponding to EP 10250841, dated Aug. 27, 2010; (6 pages).
Extended European Search Report corresponding to EP 11250183, dated Jun. 8, 2011; (6 pages).
See "Surgical Stapler Information," "Other Data," at www.fda.gov/cdrh/surgicalstapler/othersub.--data.html, from update of Jul. 21, 2004; (2 pages).
Notification of the Third Office Action for CN 201010159641.3 dated Dec. 3, 2014.
Japanese Office Action dated Mar. 31, 2015 for JP 2014-085230.
Notification of the Fourth Office Action for Appln. No. 201010159641.3 dated Aug. 18, 2015.
Japanese Office Action dated Nov. 11, 2015 for JP 2014-085230.
Canadian Office Action for CA 2,699,134 dated Feb. 9, 2016.
Japanese Notice of Final Rejection for JP 2014-085230 dated Mar. 18, 2016.
Japanese Office Action dated Feb. 22, 2017 in corresponding Japanese Patent Application No. 2014-85230, together with English translation 29 pages.
Japanese Office Action dated Apr. 10, 2017 in corresponding Japanese Patent Application No. 2015-123679 together with English translation, 2 pages.
Chinese Office Action dated May 9, 2018 issued in corresponding Chinese Patent Appln. No. 2016101160558.
Chinese First Office Action corresponding to counterpart Int'l Appln. No. CN 2016101160558 dated Aug. 16, 2017.
Australian Examination Report dated Jul. 18, 2018 issued in corresponding AU Appln. No. 2017202913.
European Search Report dated Oct. 23, 2018, corresponding to counterpart European Application No. 18170327.3; 12 pages.

* cited by examiner

SURGICAL STAPLING APPARATUS EMPLOYING A PREDICTIVE STAPLING ALGORITHM

FIELD OF THE DISCLOSURE

The present disclosure relates to a surgical stapler for implanting mechanical surgical fasteners into the tissue of a patient, and, in particular, to a surgical stapler which is powered by a motor for firing surgical fasteners into tissue and a control system for determining one or more conditions related to the firing of the surgical fasteners and controlling the stapler in response to one or more sensed feedback signals.

BACKGROUND INFORMATION

Some surgical procedures require the compression, e.g., clamping, of a patient's tissue. Such procedures may include, e.g., anastomosing, stapling, and resecting of tissue. For example, where cancerous tissue is identified in a patient's gastrointestinal tract, the cancerous tissue may need to be surgically removed. Where, for example, the cancerous tissue is located on the colon and is accessible by surgical instrumentation, the surgeon may make an incision in the patient's abdomen to allow access to the bowel. The surgeon may then use a linear cutting and stapling device, such as that described in U.S. patent application Ser. No. 12/235,362 (now U.S. Pat. No. 7,963,433), which is expressly incorporated herein in its entirety by reference thereto, to cut and staple the colon tissue on opposite sides of the cancerous portion to be removed. In this procedure, the colon is externally clamped (e.g., between opposed jaws) to compress the tissue. While the tissue is compressed, a cutter and a stapler are activated to make a linear cut and apply typically two linear rows of staples in the areas adjacent the cut. The stapling thus closes both open ends of the portion of the bowel to be removed, as well as providing a temporary closure of the two cut ends of the bowel. This closure limits exposure of the surrounding tissue to the interior of the bowel, thus limiting the risk of infection. After the cutting and stapling procedure, the cancerous portion of tissue may be removed from the patient's body.

After the resection of the cancerous tissue, the surgeon may employ an anastomosing and stapling device, e.g., a circular stapler/cutter, such as that described in U.S. patent application Ser. No. 10/785,682 (now U.S. Pat. No. 7,342,983), which is expressly incorporated herein in its entirety by reference thereto. During this procedure a head portion is positioned within the colon adjacent one of the cut ends and a base or shaft portion is positioned within the colon adjacent the other cut end. The head portion and the base portion may be coupled via a shaft and/or cable that extends out of one cut end and into the other. Via this coupling, the surgeon is able to actuate the anastomosing and stapling device to draw the head portion and the base portion together. After the two cut ends of the colon contact each other, the actuation continues such that the two portions of the colon are clamped together at an annular area of contact. While clamped, the anastomosing and stapling device may be further actuated to apply an annular ring of staples into the compressed tissue. The device may also cut excess tissue disposed within the colon. The head portion and the base portion are then moved apart and the anastomosing and stapling device removed from the patient.

To achieve effective stapling in the above procedures, the tissue must be compressed to the extent that there is an adequately small tissue gap, e.g., one millimeter, between the faces of the tool. If the clamping structures of the instrument are exposed to enough force, maintaining a uniform target tissue gap across the length of tissue to be stapled may be difficult or even impossible. For example, where the clamping structures are cantilevered jaws of a linear stapler, the jaws may splay outwardly from each other under high clamping forces. Where one or both of the jaws splay in this manner, the tissue gap typically increases toward the distal ends of the jaws. Where this tissue gap exceeds an acceptable range, staples may not adequately close the tissue to prevent contamination. This may be result from, e.g., the initial stapled gap being too large and/or failure of the staple (e.g., separation from one or more of the portions of stapled tissue) due to improper formation resulting from, e.g., too large a gap between a staple pusher and an anvil that closes the staple.

Such problems with the stapling procedure may lead to contamination of tissue (e.g., contamination of tissue adjacent the bowel with bowel contents), which may contribute to infection and/or sepsis. Such problems with the stapling procedure may also lead to, e.g., failure of the anastomosis (e.g., where the stapled tissues separate) and/or excessive bleeding due to improper tissue closure. Moreover, these problems may require additional, repeated, and/or prolonged surgery along with any increased risks associated therewith. As reported by the United States Food and Drug Administration (see "Surgical Stapler Information," "Other Data," at http://www.fda.gov/cdrh/surgicalstapler/other_data.html, last updated Jul. 21, 2004), infection, sepsis, anastomosis failure, and bleeding are substantial problems that arise in stapling procedures and may potentially lead to serious injuries, or even death, to some patients. It is thus desirable to minimize these problems.

Moreover, when performing the compression, a constant closing rate (e.g., the closing rate between jaws of a linear stapler or between the head and base portion of a circular stapler/cutter) may exert a high level of power into the clamped tissue. This high level of power may result in excess tissue trauma. It is thus desirable to limit this trauma, e.g., by effectively controlling the power applied to the tissue. Further, it is desirable to determine whether the tissue to be clamped is compressible.

U.S. Patent Application Publication No. 2009/0057369 (now U.S. Pat. No. 7,959,050) describes a device that uses continuous measurements from a linear force switch housed in an anvil neck. The switch is calibrated to activate when a given load is applied. The given load is set to correspond to a desired pressure that is to be applied to the particular tissue before stapling can occur. Interfacing this switch with a processor provides firing of staples only within a compression range. Such devices and control methods do not allow for a continuous closure or monitoring of power going into the compressed tissue.

Further, it is desirable to monitor and track structural fatigue in clamping members in a simple and reliable manner.

It is additionally desirable to identify proper staple filing in a simple and reliable manner.

SUMMARY

In an aspect of the present disclosure, a surgical device is provided. The surgical device includes a tool assembly having an anvil assembly and a cartridge assembly configured to grasp tissue therebetween where the cartridge assembly includes a plurality of surgical fasteners. A motor is configured to fire one or more surgical fasteners and a sensor is configured to determine a first parameter of the tool assembly. The device also includes a control system configured to adjust a second parameter of the motor used to fire the one or more surgical fasteners based on the first parameter detected by the sensor.

In some embodiments, the first parameter is a clamp force between the anvil assembly and the cartridge assembly. In some embodiments, the second parameter is a firing speed of the motor or a wait time between a clamping state of the surgical device and a firing state of the surgical device.

The sensor used to detect the first parameter may be a strain gauge.

In some embodiments, the surgical device may include a display configured to display a predicted firing speed of the surgical device.

In another aspect of the present disclosure, a method for determining a firing speed of a surgical device is provided. The surgical device includes a tool assembly with a cartridge assembly and an anvil assembly and a motor configured to actuate the tool assembly. In the method, a clamp force between the cartridge assembly and the anvil assembly is determined and a firing speed of the motor is determined based on the clamp force.

In some embodiments, the firing speed of the motor is displayed to a user.

The above and other aspects, features, and advantages of the present disclosure will become more apparent in light of the following detailed description when taken in conjunction with the accompanying drawings in which.

Figure 6A:
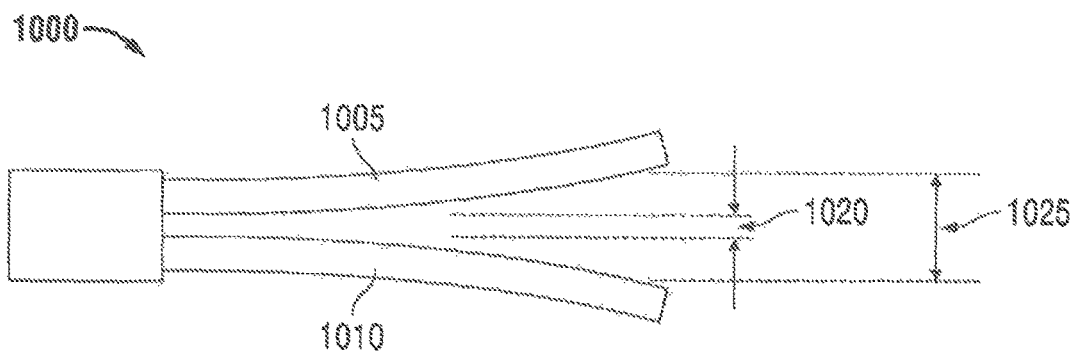
Figure 6B:
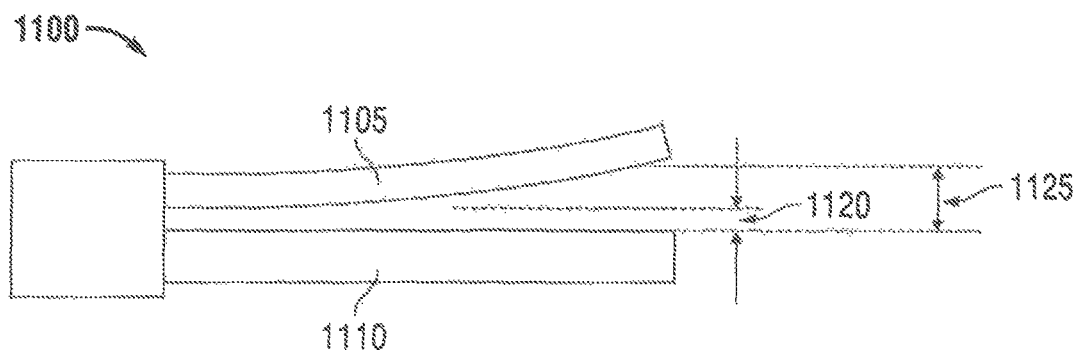
Figure 8:
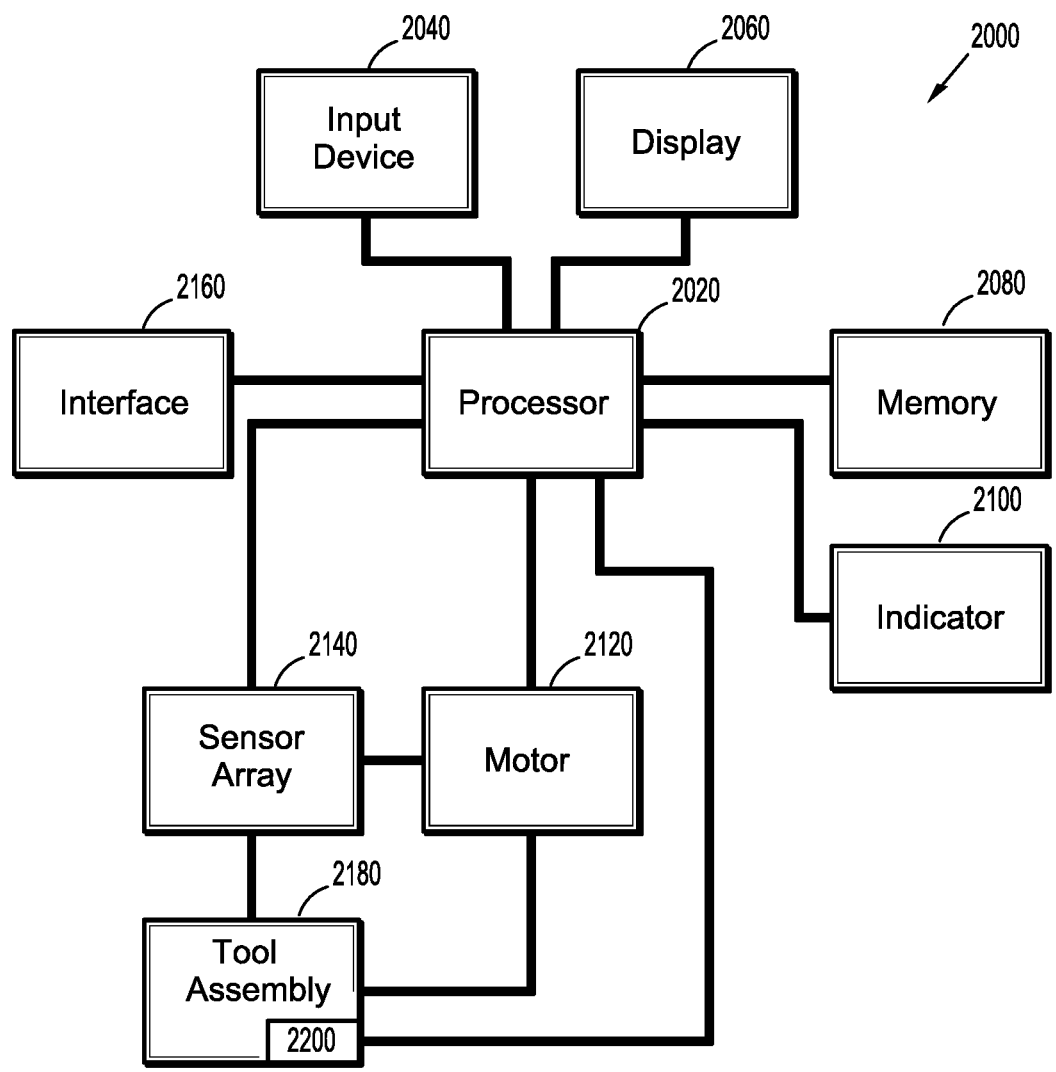
Figure 9:
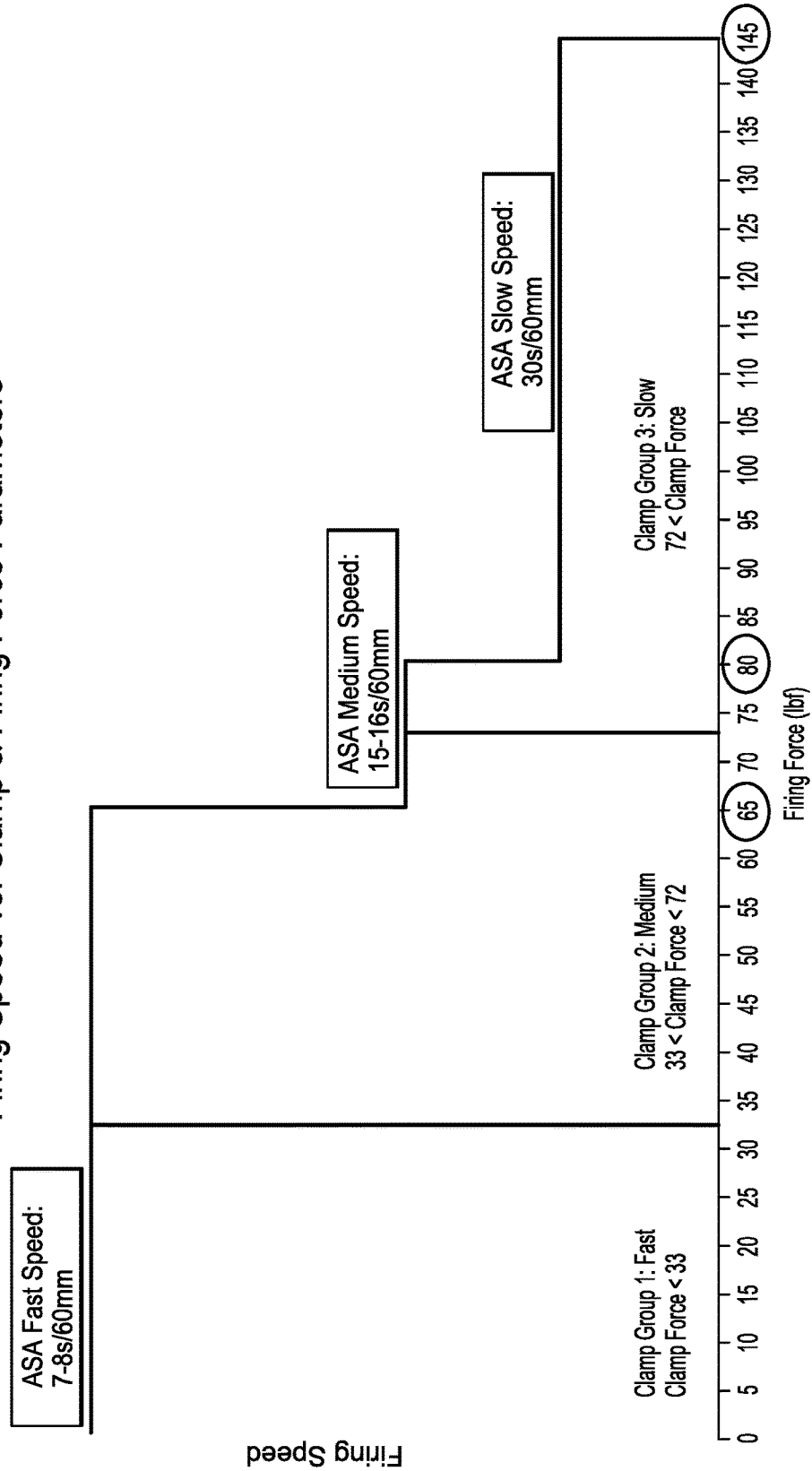

FIGS. 6a and 6b schematically illustrate a splaying effect of jaws of a prior art stapling device;

FIGS. 7a to 7d illustrate current profiles associated with different prior art stapling events;

FIG. 8 is a system block diagram of a powered surgical instrument according to an embodiment of the present disclosure; and FIG. 9 is a chart depicting the relationship between a firing speed of the powered surgical instrument of FIG. 8 versus the clamp and firing force parameters.

DETAILED DESCRIPTION

Particular embodiments of the present disclosure are described hereinbelow with reference to the accompanying drawings; however, it is to be understood that the disclosed embodiments are merely exemplary of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

Like reference numerals may refer to similar or identical elements throughout the description of the figures. As shown in the drawings and described throughout the following description, as is traditional when referring to relative positioning on a surgical instrument, the term "proximal" refers to the end of the apparatus which is closer to the user and the term "distal" refers to the end of the apparatus which is farther away from the user. The term "clinician" refers to any medical professional (e.g., doctor, surgeon, nurse, or the like) performing a medical procedure involving the use of embodiments described herein.

The embodiments described herein may be used in a surgical instrument, e.g., a linear surgical stapler, a circular surgical stapler, or a right-angle linear cutter, that gathers information prior to firing a fastener (e.g., staple or clip) to optimize fastener formation and lower maximum forces on the instrument during firing.

During compression of a patient's tissue, hydraulic effects are present as a result of the composition (e.g., the presence of fluids, etc.) of the tissue. In this regard, hydraulic resistance may be measured and used as feedback for the closing of the clamping elements.

When clamping the patient's tissue, forces exerted through the clamping device, e.g., a linear stapler, and the tissue may reach an unacceptably high level. For example, when a constant closure rate is employed, the force may become high enough to cause excess trauma to the clamped tissue and may cause deformation in the clamping device such that an acceptable tissue gap is not maintained across the stapling path. For example, an acceptable tissue gap may be in the range of, e.g., 1 mm.+−0.0.4 mm, $$1\ mm_{-0.3}^{+0.4} mm$$

(0.7 mm to 1.4 mm), etc. Referring to prior art FIGS. 6a and 6b, linear surgical staplers 1000 and 1100 are schematically illustrated when exerting a clamping force on a section of tissue.

As illustrated, the high level of force exerted by the jaws of the staplers 1000 and 1100 results in a splaying effect, which has been exaggerated in prior art FIGS. 6a and 6b for illustration purposes. Referring to prior art FIG. 6a, a pair of opposed jaws 1005 and 1010 form a target tissue gap 1020 only at a proximal portion, whereas the distal ends of the jaws 1005 and 1010 are splayed outwardly away from each other, resulting in an expanded tissue gap 1025 at a distal portion. This splaying causes the jaws 1005 and 1010 to deviate from a parallel alignment, which may lead to an unacceptably large tissue gap where staples are applied toward the distal ends of the jaws 1005 and 1010, which in turn may result in the aforementioned difficulties, such as, e.g., leakage, contamination, and failed staple connections. This splaying results from exceeding a yield force that causes the jaws to deviate from the parallel alignment relative to each other.

Prior art FIG. 6b shows a comparable effect, but where the splaying occurs primarily in a first jaw 1105 that is structurally weaker than a second jaw 1110. This again leads to an unacceptably large tissue gap 1125 that substantially exceeds a target tissue gap 1120.

Figure 1:
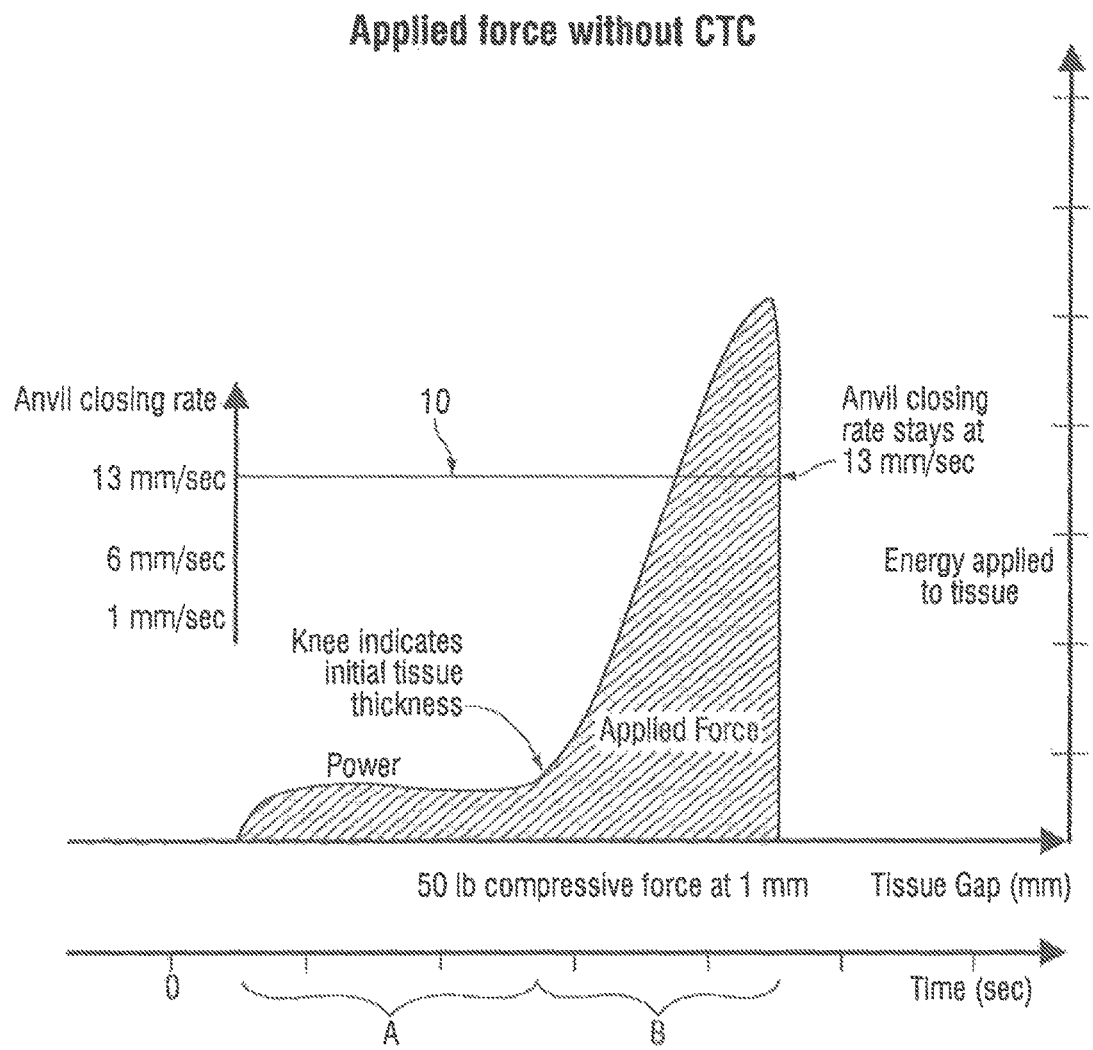
FIG. 1 is a prior art graph illustrating the power applied to tissue during compression at a constant anvil closing rate.

FIG. 1 is a prior art graph illustrating the power applied to tissue during compression at a constant anvil closing rate. The compression begins at an initial open state, wherein the clamping members or elements move a distance prior to compression of the tissue therebetween. Region A represents the time during which the clamping elements move from the initial open state to the beginning of tissue compression and region B represents the time period during which the tissue is compressed from an initial thickness to a target thickness, in this case 1 mm tissue thickness (corresponding to a 1 mm tissue gap between the clamping elements). Regions A' and B' are delineated by a "knee" that indicates the beginning of the compression with the tissue at its initial thickness. The power, and in turn the force, imparted into the tissue rises sharply with respect to time until reaching a peak value. Line 10 indicates the closing rate of the clamping members (indicated in prior art FIG. 1 as Anvil Closing Rate), which is constant between the initial open state and the target tissue gap of 1 mm. The hatched area under the power curve indicates the total energy exerted during the clamping procedure.

Figure 2:
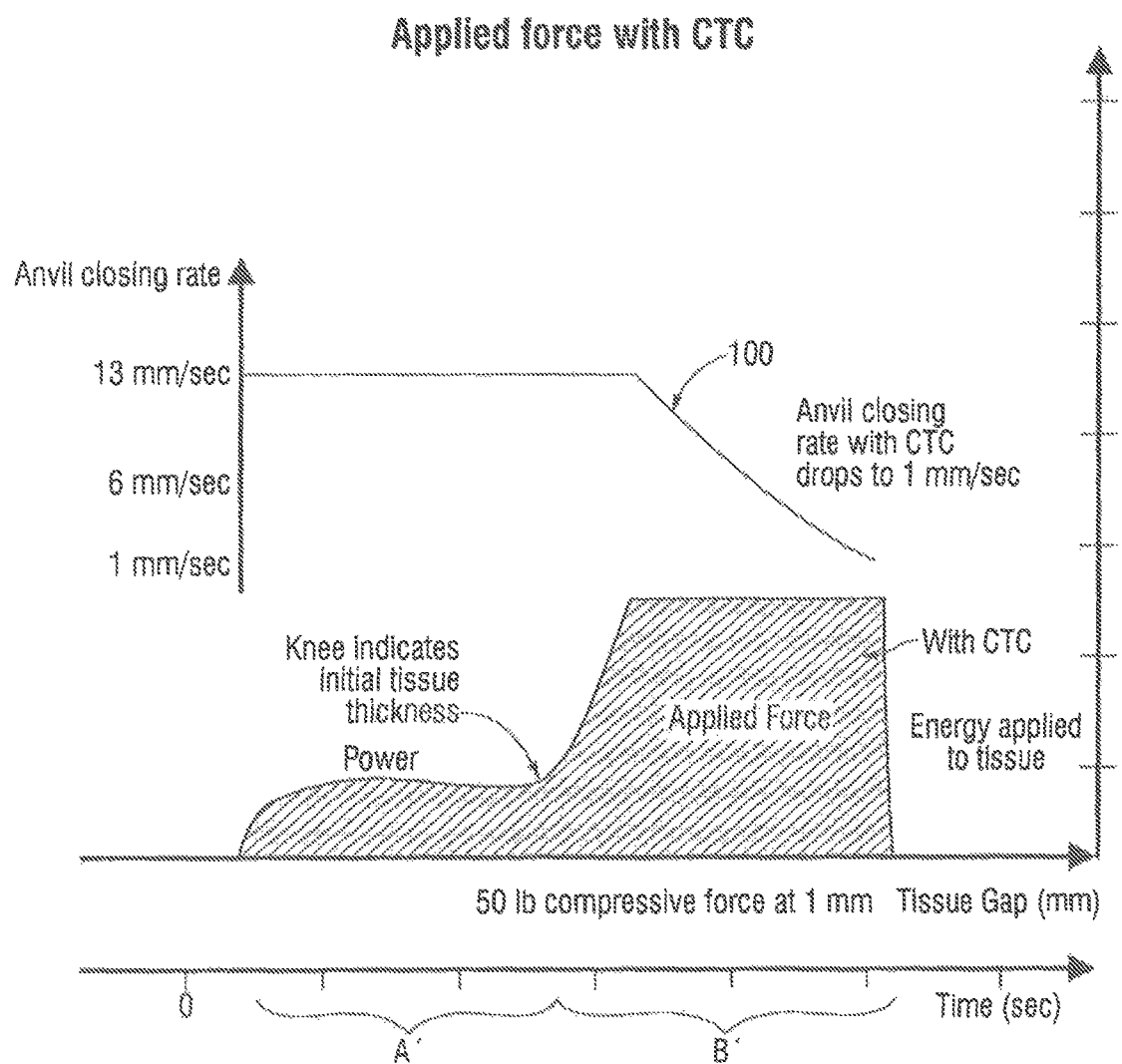
FIG. 2 is a prior art graph illustrating the power applied to tissue during compression according to an embodiment of the present disclosure.

FIG. 2 is a prior art graph illustrating the power applied to tissue during compression according to an example embodiment of the present disclosure. As with the device and method corresponding to the prior art graph of FIG. 1, the compression as illustrated in prior art FIG. 2 begins at an initial open state, in which the clamping members or elements move a distance prior to compression of the tissue therebetween. Region A' represents the time during which the clamping elements move from the initial open state to the beginning of tissue compression, and region B' represents the time period during which the tissue is compressed from an initial thickness to a target thickness, in this case 1 mm tissue thickness (corresponding to a 1 mm tissue gap between the clamping elements). A' and B' are delineated by a "knee" that indicates the beginning of the compression with the tissue at its initial thickness. During the period designated A', the clamping elements close at a constant rate of, e.g., 13 mm/sec. It should be appreciated, however, that any appropriate rate may be employed and need not be constant over the entire period A'. The hatched area under the power curve indicates the total energy exerted during the clamping procedure.

In contrast to prior art FIG. 1, prior art FIG. 2 illustrates that it is determined that the power applied to the tissue is increasing and, at a certain level, the closing rate is decreased, in this example, from 13 mm/sec to 1 mm/sec, effectively increasing the time required to compress the tissue and decreasing the power applied to the tissue. The closing rate is illustrated in prior art FIG. 2 as line 100. In this example, the power applied to the tissue is held constant, although it should be appreciated that according to certain example embodiments, the power may fluctuate.

Figure 3:
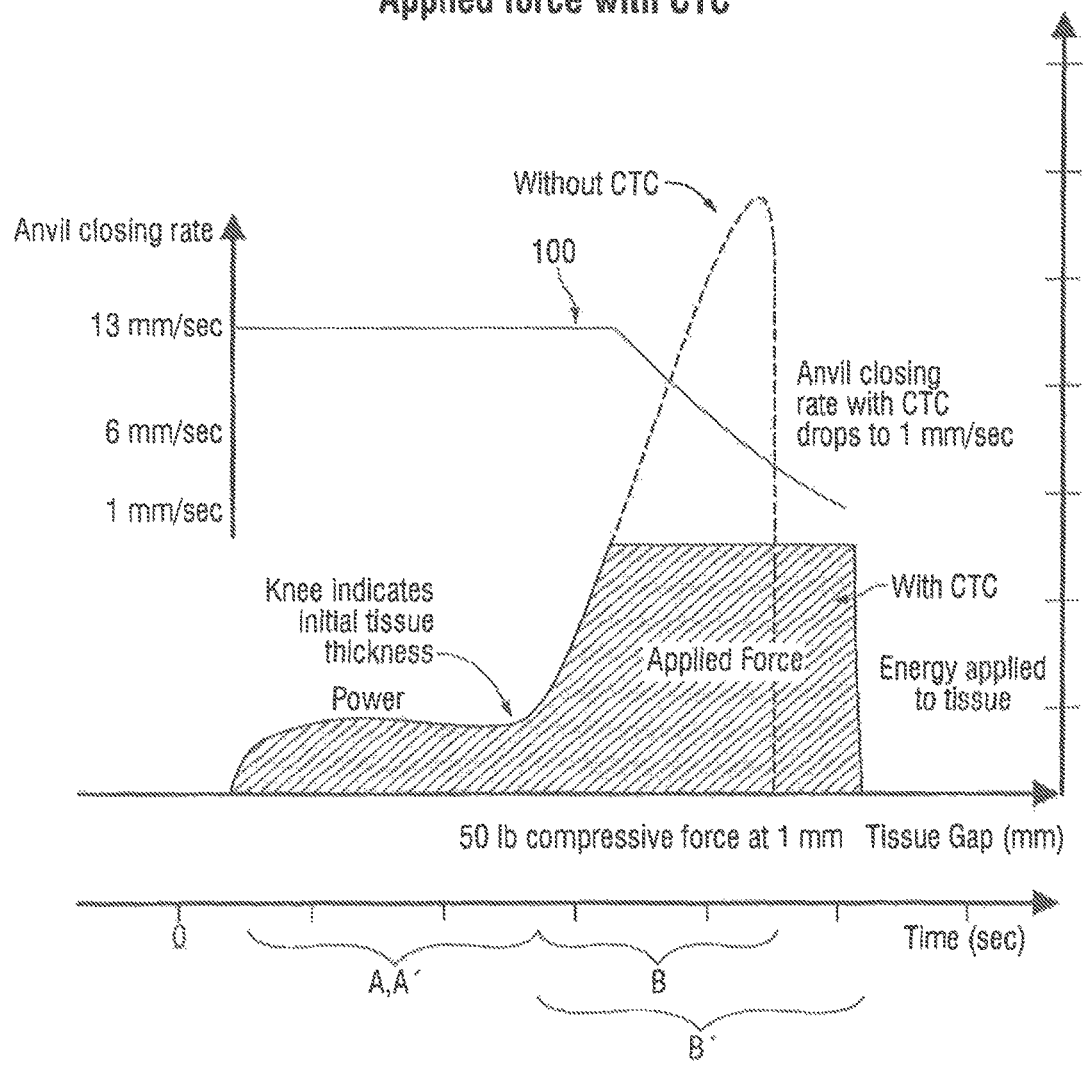
FIG. 3 is a superposition of the prior art graphs of FIG. 1 and FIG. 2.

FIG. 3 is a superposition of the prior art graphs of FIG. 1 and FIG. 2. In contrast to the system and method reflected in prior art FIG. 1, the peak power imparted into the tissue according to prior art FIG. 2 is much lower. Based on the imparted power, the force exerted by the surgical device (or a parameter related to or proportional to the force) may be calculated. In this regard, the power may be limited such that the force exerted through the surgical device, e.g., through the jaws of a linear stapler, do not exceed a yield force or pressure that results in splaying of the jaws such that the tissue gap is not within an acceptable range along the entire stapling length when in the fully closed position. For example, the jaws should be parallel or close enough to parallel that the tissue gap remains within the acceptable or target range for all staple positions along the entire length of the jaws. Further, the limitation of the exerted power avoids, or at least minimizes, trauma or damage to tissue.

In this example, the total energy exerted in the prior art method of FIG. 1 is the same as the total energy exerted in the prior art method of FIG. 2, i.e., the areas under the power curves of prior art FIGS. 1 and 2 are the same or substantially the same. The difference in the power profiles utilized is, however, substantial, as the peak power is much lower in the example of prior art FIG. 2 as compared to prior art FIG. 1.

The limiting of power is achieved in the example of prior art FIG. 2 by slowing the closing rate, as illustrated by line 100. It is noted that the compression time B' is longer than the closing time B. As illustrated in prior art FIGS. 1 to 3, a device and method that provides a constant closure rate achieves the same 50 lb. of compressive force at the same 1 mm tissue gap as the device and method reflected in connection with prior art FIG. 2. While the device and method that provide for a constant closure rate (FIG. 1) may achieve the compressive force at the desired tissue gap in a shorter time period as compared with prior art FIG. 2, as illustrated, e.g., in prior art FIG. 1, this results in the spike in power applied to the tissue. In contrast, the example embodiment illustrated, e.g., in connection with prior art FIG. 2, begins slowing the rate of closure to limit the amount of power applied to the tissue below a certain level. By limiting the power applied to the tissue, tissue trauma may be minimized with respect to the system and method reflected in prior art FIG. 1.

According to example embodiments, the device and method may be implemented by determining the power or force applied to the tissue by measurement of the current applied to an actuator, since the current is proportional to the torque output of the motor. In this regard, losses based on the instrument, e.g., due to friction between moving parts, etc., may be subtracted from the power applied to the driving motor to more accurately determine the power that is being imparted into the tissue. These losses to be backed out may be determined in any appropriate manner such as, e.g., testing the instrument or components of the instrument, using known qualities of the instrument or components of the instrument, and/or performing calculations based on the testing and/or known qualities. For example, the instrument may be driven in an unloaded condition to obtain a baseline measurement of power or current required to drive the instrument and its associated components. Thereafter, power or current in excess of the baseline corresponds to the power that is applied to the tissue during compression.

Where, for example, the actuator is a direct-current electric motor, the power applied to the motor may be determined based on a measurement of the current required to drive the motor. The losses due to the instrument are then backed out to determine the power imparted into the tissue during the compression. This measurement allows a source of feedback when compressing the tissue. The power applied to the motor may be continually monitored with calculations being performed on a continuous basis. This allows, for example, the power or force applied to the tissue to be accurately controlled, e.g., by adjusting the voltage going into the motor. In this example feedback control system, the consumed current would be the feedback, with the voltage being adjusted to achieve a desired current. The example illustrated in the prior art graph of FIG. 2 uses this control system to reduce the rate of closure when the determined power hits a particular level, e.g., a predetermined power level selected to prevent unacceptable levels of tissue trauma.

Figure 4:
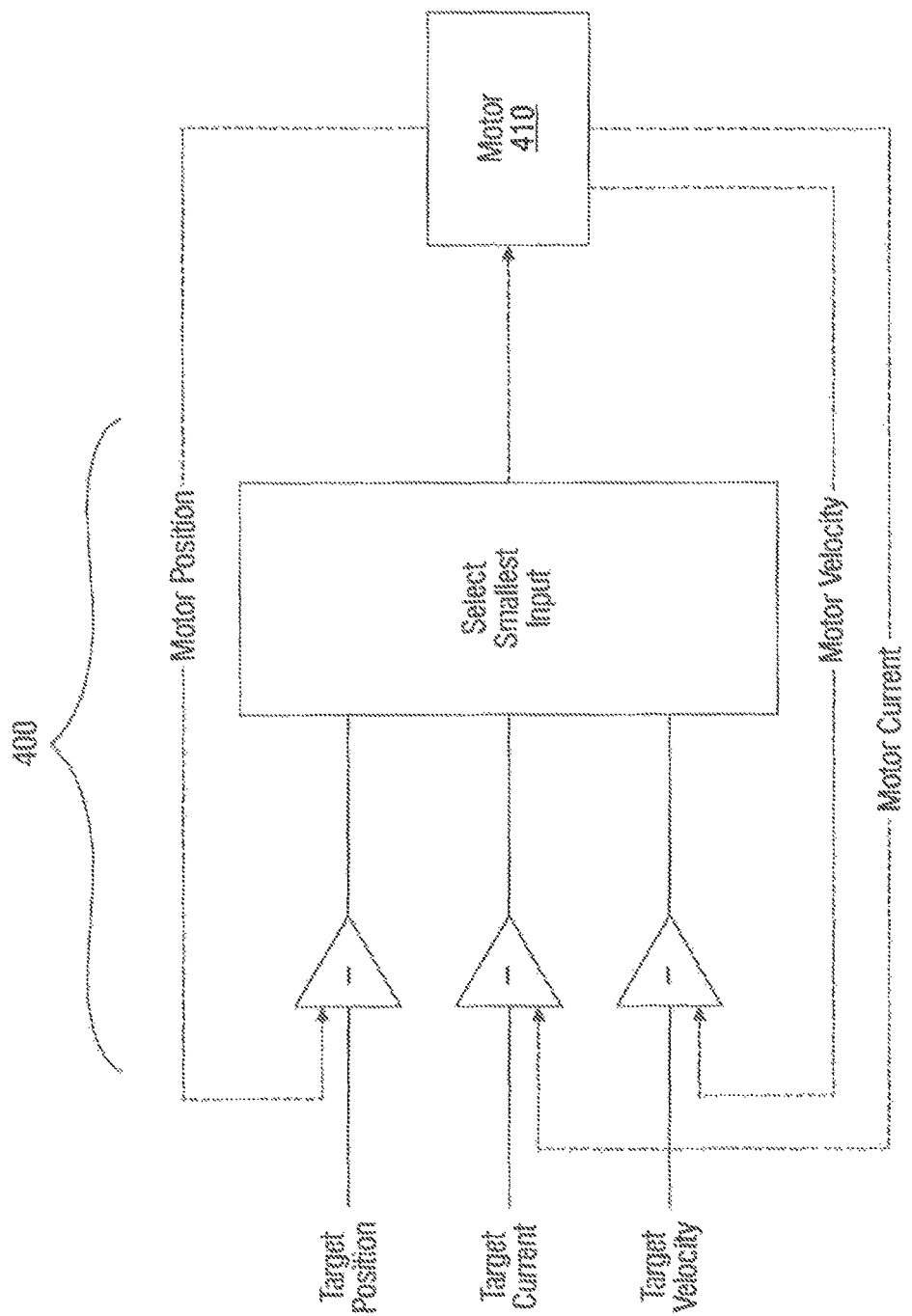
FIG. 4 is a schematic illustration of a prior art control system.

FIG. 4 is a schematic illustration of a prior art control system. A controller 400 controls a motor 410 that drives a clamping operation, e.g., clamping of the jaws of a linear surgical stapler. A target position, a target current, and a target velocity are input into the controller 400, e.g., by a particular control program and/or manual input by a surgeon or operator. The controller 400 receives motor position, motor velocity, and motor current signals as feedback for controlling the motor 410. As discussed in greater detail below, the controller 400 according to this example selects the smallest input for controlling the motor 410.

Figure 5:
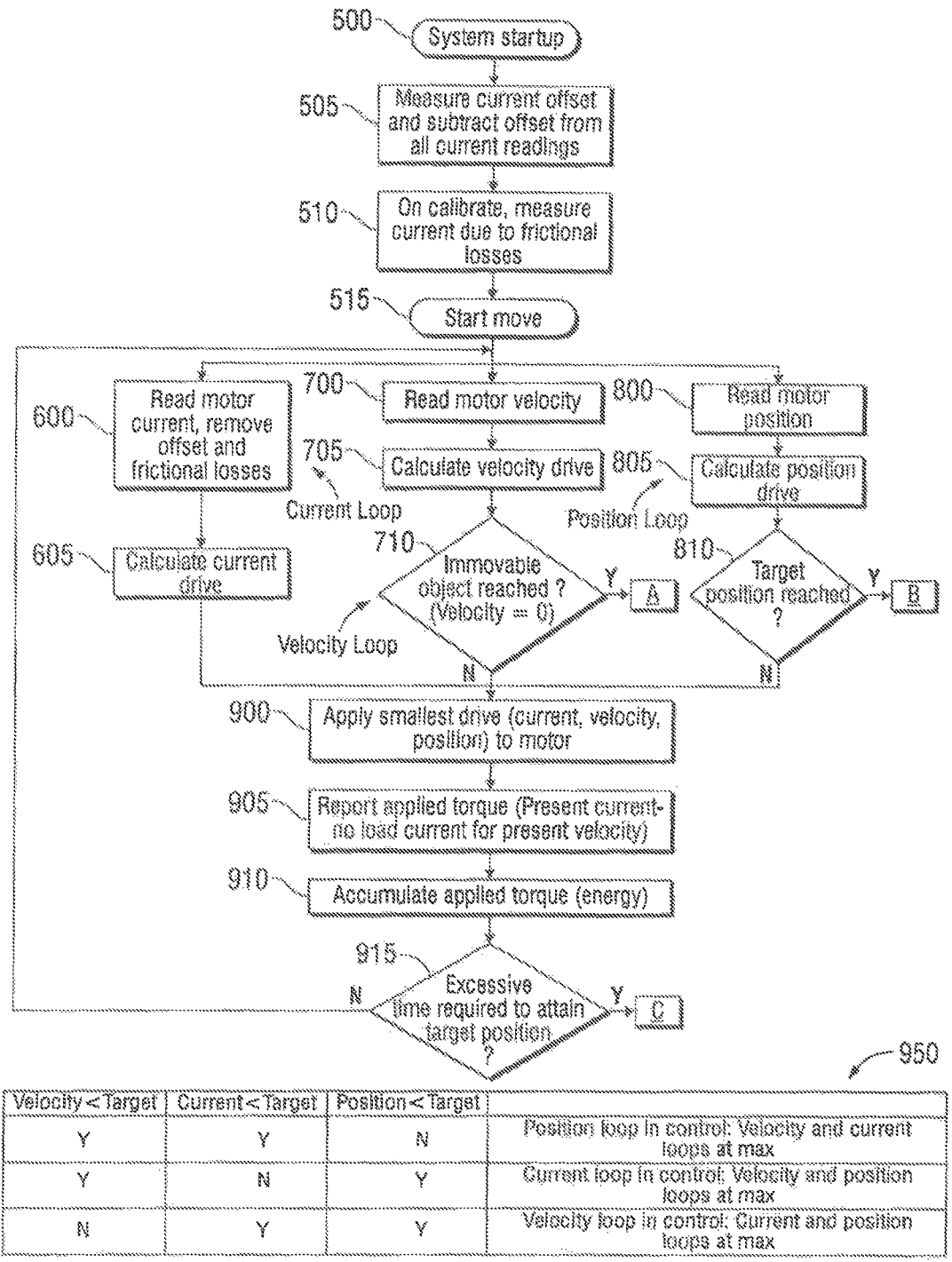
FIG. 5 is a flowchart illustrating a prior art method.

FIG. 5 is a flowchart illustrating a prior art method. System startup occurs at 500. After system startup, current offset is measured and set to be subtracted from all current readings so that all readings are taken from a zero or near-zero baseline. At 510, calibration occurs, including measuring current due to frictional losses, e.g., friction in the motor and the drive components that convert the rotational force of the motor into the clamping force exerted through the instrument, e.g., the force exerted through the jaws of a linear stapler. The calibration may be performed by measuring the current corresponding to different motor speeds under a no-load condition, i.e., during unobstructed movement. It should be appreciated that the offset measurement and calibration may be performed every time the system starts up and/or the values obtained may be stored to be used in subsequent procedures using the same equipment. For example, the control system may require re-measuring of these values after a given time period, number of uses, and/or number of system startups.

After calibration, the clamping procedure may begin. When the tissue to be clamped is disposed in the clamping portion of the surgical instrument, movement is started at 515. The exemplary method then performs a current loop, a velocity loop, and a position loop. These loops need not be performed in any particular order and two or all three of the loops may be performed simultaneously, or substantially simultaneously, in some examples.

For the current loop at 600, motor current is read, e.g., according to the signal of a current sensor arranged to sense the current driving the motor. The offset and frictional losses, determined at 505 and 510, are removed or subtracted out. In this manner, the portion of the current that is applied in response to the tissue clamping is determined. At 605, a current drive is calculated using a current drive formula. For example, the current drive may be determined by $K_1*$(target current-motor current), where $K_1$ is selected based on desired control performance for controlling the motor current.

For the velocity loop at 700, the motor velocity is determined. The velocity is determined either by reading a signal from a velocity signal or any other appropriate manner, e.g., from position and time data. At 705, a velocity drive is calculated using a velocity drive formula. For example, the velocity drive may be determined by $K_2*$(target velocity-motor velocity), where $K_2$ is selected based on desired control performance for controlling the motor velocity. At 710, it is determined whether an immovable object has been reached. In this regard, a velocity value of zero is indicative of an immovable object or obstruction being reached by the clamping device. If an obstruction has been reached, the driving of the motor is then stopped at A. Otherwise, the control continues. It should be appreciated that this determination may be made before, after, and/or at the same time as the calculation of the velocity drive.

For the position loop at 800, the motor position is read. The motor position may be determined, e.g., by an encoder or a resolver coupled to an output of the motor, or any other appropriate manner. At 805, a position drive is calculated using a position drive formula. For example, the position drive may be determined by $K_3*$(target position-motor position), where $K_3$ is selected based on desired control performance for controlling the motor position.

At 810, it is determined whether a target position has been reached. If the target position has been reached, the control loop exits at B. At B, the output to the motor may be stopped (e.g., where the tissue is clamped using drivers that are not back-drivable by residual pressures exerted by the clamped tissue or by the force of a staple being driven and formed between the clamping members) and/or the motor may be controlled to output an amount of force needed to maintain the motor at the target position, which generally corresponds to the target tissue gap in the examples described above. If the target position has not been reached, the control continues. It should be appreciated that the determination of whether the target position has been reached may be made before, after, and/or at the same time as the calculation of the position drive. Further, it should be appreciated that the relative position of the clamping elements, e.g., jaws, or any intermediate component, e.g., a driver, may be used as a positional input.

After the three control loops, the calculated current drive, velocity drive, and position drive, are compared, and the smallest drive is applied to the motor at 900. At 905, the applied torque, which is proportional to and determined from the motor current after subtracting out the offset and frictional losses, is reported. At 910, the applied torque is accumulated to calculate the energy applied to the tissue.

Chart 950 illustrates control prioritization for three different situations. In the first situation, the motor velocity and motor position are below their respective targets, while the motor position is not. In this situation, the position loop controls, while the velocity and current loops are set to maximum values. In the second situation, the velocity and position loops are below their respective targets, while the current loop is not. In this situation, the current loop controls the output, while the velocity and position loops are set to maximum values. In the third situation, the current and position loops are below their respective targets, while the velocity is not. In this situation, the velocity loop controls, while the current and position loops are at maximum values.

It is determined at 915 whether an excessive time is required to attain the target position. This determination may be made by, e.g., examining the amount of time that has elapsed up until the decision 915, a predicted total amount of time based on the elapsed time and the control profile (e.g., current, velocity, and position), and/or any other appropriate manner. If it is determined that the required time is excessive, the exemplary control method exits at C. At C, the control output to the motor may stop or another control method may be employed, e.g., to reverse the position of the motor. For example, the motor may be driven to move the jaws of a linear stapler to an open position so that the surgeon or operator may remove the surgical device or move the jaws to a different portion of tissue that may be easier to clamp. In other words, at C a request or requirement user intervention may be triggered.

If it is determined that an excessive time is not required, the control system again executes the current, velocity, and position loops at 600, 700, and 800, respectively. This loop continues until one of the events A, B, and/or C occurs to break the loop. It should be appreciated, however, that additional conditions may be implemented to break the loop, e.g., a manual override, a sensor error, etc.

Figure 7A:
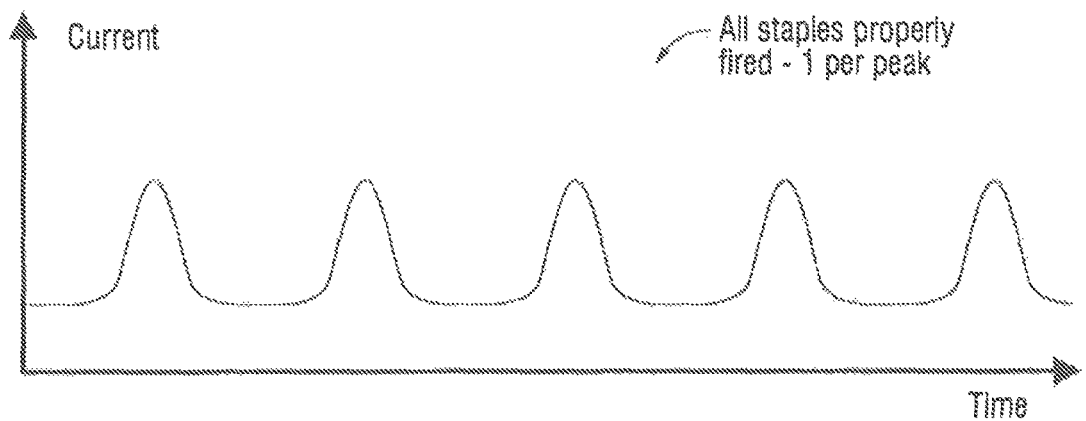

As indicated above, after the target position is reached at B, the motor may be controlled to maintain a force necessary to maintain the target position. The current driving the motor may be monitored at this stage for a variety of purposes. For example, where the device is, e.g., a surgical stapler, a profile of the measured current may be used to identify whether all of the staples of a staple cartridge have fired. Prior art FIG. 7a illustrates an expected current profile during a stapling procedure as a driver, e.g., a wedge, sequentially drives five staples. It should be understood that any number of staples may be provided and the firing of five staples is for illustration purposes. The peaks in the current measurement correspond to the increased force or power necessary to hold the tissue gap with the staple be forced between the clamping elements, e.g., the jaws of a linear stapler. If the firing is initiated and a current profile that closely resembles prior art FIG. 7a results, it may be determined that all of the staples properly driven or fired.

Figure 7B:
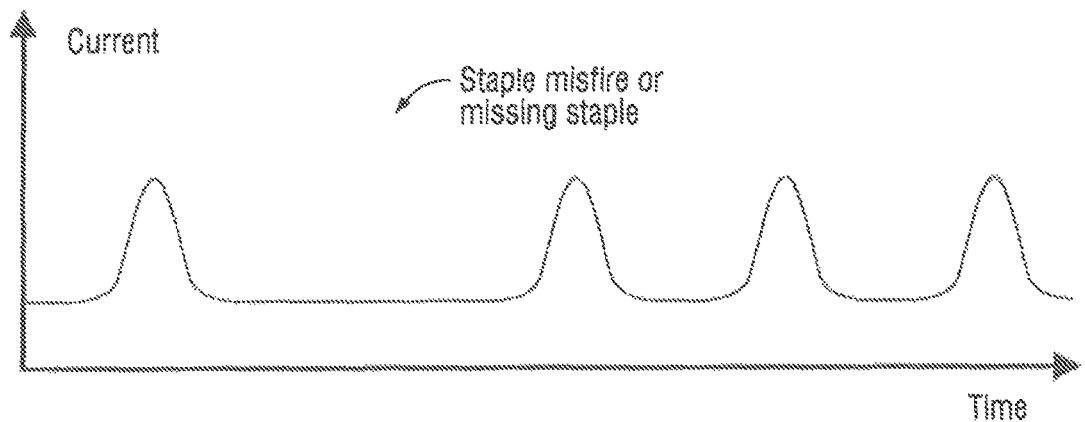

If the staple driving procedure is initiated and results in a current profile as illustrated in prior art FIG. 7b, it may be determined from the lack of a peak that the second staple position was not properly driven or fired, e.g., due to a misfire or a missing staple from the staple cartridge. A misfire may similarly be shown, e.g., when a current peak is present, but substantially lower than expected.

Figure 7C:
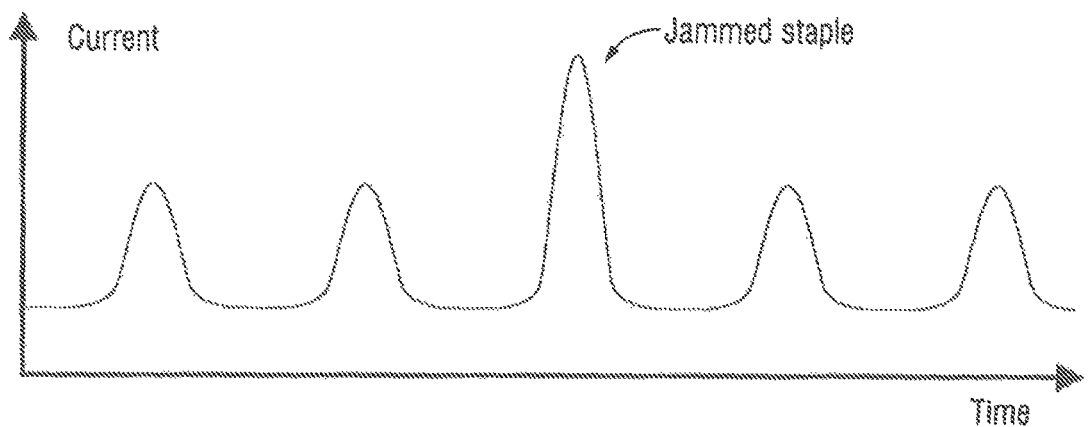

If the staple driving procedure is initiated and results in a current profile as illustrated in prior art FIG. 7c, it may be determined that the staple in the third staple position jammed in some manner, resulting in the higher peak current measurement.

Figure 7D:
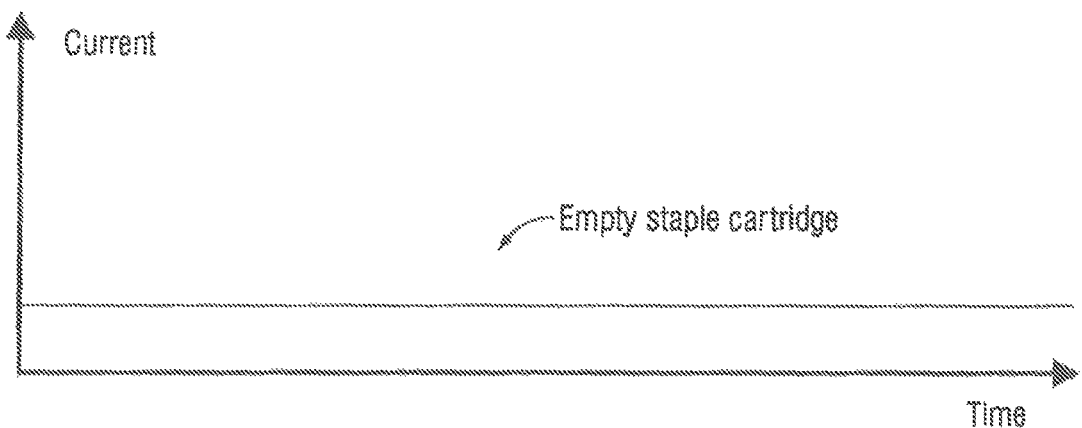

If the staple driving procedure is initiated and results in a current profile as illustrated in prior art FIG. 7d, it may be determined that the staple cartridge is empty or that a staple cartridge is not present.

If any of these unexpected events occur, the control system may alert the user, e.g., by emitting an audible alarm and/or displaying an error message on a computer screen. The control system also may abort the staple firing, and or enter a different control algorithm.

Moreover, a profile of the current measurements may be used to monitor and track structural fatigue in at least one of the clamping members, e.g., by comparing to a normal current or motor signature. In this regard, a current profile may indicate, e.g., flexure due to plastic deformation resulting from fatigue failure. Further, the current profile may be used to track accumulated fatigue by determining the amount of force and the number of cycles exerted by a clamping member.

It should be appreciated that example methods according to the present disclosure may be implemented using any appropriate control system, e.g., a digital and/or analog control system, which may be integrated into the medical device or may be remotely located, whereby control and feedback signals are communicated via, e.g., a wireless or wired interface. The control system may have a display output, e.g., a monitor, and/or inputs to communicate with, e.g., a surgeon. The display output may display data relevant to the procedure including, e.g., the current closing rate, compressive force, and/or tissue gap. The control system may run predefined control programs or algorithms that may be pre-selected for the particular device. The control system may additionally or alternatively ask for inputs from the operator to define the parameters of the tissue compression control.

Further, the compressibility of the tissue may be determined by examining the current applied to the motor as compared with the closing rate. For example, if the measured current is very high when using a low closing rate, the tissue is less compressible than situations where the current is low for a higher closing rate.

While a tissue gap of 1 mm is mentioned above as an example of a desired tissue gap appropriate for tissue stapling, it should be appreciated that instead of an absolute distance measurement for the gap, alternative gap parameters may be provided. For example, one or more optical sensors may be provided to measure blood flow across one or more staple lines as a measure of desired tissue gap. Furthermore, oxygen saturation may be used in connection with the determination of the desired tissue gap. Moreover, the ratio of compressed to uncompressed tissue, e.g., based on the power applied to the tissue at the knee in the prior art graphs of FIGS. 1 and 2, may form the basis of the desired tissue gap.

FIG. 8 is a schematic illustration of a control system 2000 according to an exemplary embodiment of the present disclosure. Control system 2000 includes a processor 2020, an input device 2040, a display 2060, a memory 2080, an indicator 2100, a motor 2120, a sensor array 2140, an interface 2160, and a tool assembly 2180.

Processor 2020 may be an integrated circuit or may include analog and/or logic circuitry that may be used to: execute instructions according to inputs provided by the input device 2040 or sensor array 2140, execute instructions according to a program provided in memory 2080; and/or control motor 2120 thereby controlling the tool assembly 2180 to perform any number of functions, including, but not limited to clamp tissue therebetween and/or fire the surgical fasteners.

Input device 2040 may include a keyboard, a touch-screen input device, switches and/or buttons to control operation of the surgical instrument (not shown). Input device 2040 may be used to; select between tissue management modes; control tool assembly 2180; apply a staple or clamp; and input tissue properties such as tissue type and/or disease.

Display 2060 may include a liquid crystal display, a light-emitting diode (LED) display or the like. Display 2060 may output a status of the surgical instrument, measured tissue properties, number of surgical fasteners applied, etc.

Control system 2000 may also include an indicator 2100 that may include at least one light emitting diode (LED) to indicate whether a tissue gap range, between an anvil assembly and cartridge assembly of tool assembly 2180, has been met.

Sensor array 2140 is configured to measure current (e.g., ammeter), voltage (e.g., voltmeter), proximity (e.g., optical sensors), temperature (e.g., thermocouples, thermistors, etc.), and force (e.g., strain gauges, load cells, etc.) to determine loading conditions on the tool assembly 2180. During operation of the instrument, it is desirable to know the forces being exerted by the instrument on the target tissue during the approximation process and during the firing process. Detection of abnormal loads (e.g., outside a predetermined load range) indicates a problem with the instrument and/or clamped tissue which is communicated to the user.

Memory 2080 may be a volatile type memory (e.g., random access memory (RAM)) and/or non-volatile type memory (e.g., flash media, disk media, etc.) that stores programs or sets of instructions for the operation of the surgical instrument. Such programs may include a number of tissue management modes that perform a controlled tissue compression (CTC) operation that may be used to clamp tissue in order to apply a staple or clip to the tissue grasped by tool assembly 2180 as disclosed in U.S. Publication No. 2012/0211542 A1, which is herein incorporated by reference. Memory 2080 may also store correlation tables to correlate tissue type and disease type to the requisite tissue gap range (e.g., 0.7 mm to 1.4 mm) and firing parameters that need to the achieved to successfully apply a staple or clip to tissue. Memory 2080 also stores a predictive algorithm for controlling the firing speed of the motor 2120.

Control system 2000 may also include an interface 2160 that may be removably coupled to an external computer or network via conventional means. Processor 2020 may transmit or receive information via interface 2160 to or from the external computer or network.

Tool assembly 2180 may be a reload (not shown) or end effector (not shown). Tool assembly includes a cartridge assembly (not shown) and an anvil assembly (not shown) used to clamp tissue. The tool assembly 2180 applies a clamp force to the tissue grasped between the cartridge and anvil assemblies during a clamp stage. As will be discussed below, the clamp force is used by a predictive algorithm to adjust the firing parameters to optimize staple formation and lower maximum forces on the system during firing.

Tool assembly 2180 includes a sensor 2200, e.g., a strain gauge, which measures the clamp force on the clamped tissue and provides the clamp force data in the form of A/D counts, current, or force. Based on the clamp force data, the processor 2020 employs a predictive algorithm to adjust parameters of the surgical instrument such as firing speed, a wait time allocated between a clamp stage and a firing stage, and/or limitations for adjusting the maximum and minimum loads on the surgical instrument.

During operation of the surgical instrument, the thicker the target tissue, the greater the clamp force is needed to achieve an effective predetermined tissue gap between the cartridge assembly and the anvil assembly of tool assembly 2180 for proper staple formation. In order to optimize the staple formation, processor 2020 predicts a firing speed using the predictive algorithm based on the clamp force data as shown in prior art FIG. 3. For example, for a 60 mm staple, when the clamp force is less than 33 lbf, the processor 2020 predicts a firing speed of 7-8 seconds for a staple line of 60 mm. Alternatively, when the clamp force is greater than 72 lbf, the processor 2020 predicts a firing speed of 30 s for a staple line of 60 mm. Further, because the firing force is proportional to the firing speed, by utilizing a slower firing speed, the maximum force applied to the instrument may be lowered.

In some embodiments, display 2060 displays the predicted firing speed to a clinician. The clinician may then make a decision based on the predicted firing speed as to whether the clinician is using the correct tool assembly 2180. For instance, if a clinician inadvertently selects an incorrect tool assembly, the clamp force applied to the target tissue may be incorrect for the target tissue. By viewing the predicted firing speed and knowing the type of tissue being targeted, the clinician may be able to determine that the selected tool assembly is incorrect for the target tissue.

During a firing stage, the processor 2020 uses the predicted firing speed to control motor 2120 to fire the surgical fasteners at the predicted firing speed. As discussed above, the firing speed is reduced for thicker tissue to optimize staple formation and reduce the maximum force applied to the instruments described above.

Additional information may also be used to optimize the firing parameters of the surgical instrument. For example, sensor array 2140 may measure a current draw from a power source (not shown) or motor 2120. Sensor array 2140 may also determine a reload type, instrument type, patient biometric information, temperature, or any additional information that may be inputted, gathered and/or stored in the surgical instrument or tool assembly 2180.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing FIGS. are presented only to demonstrate certain examples of the disclosure. Other elements, steps, methods and techniques that are insubstantially different from those described above and/or in the appended claims are also intended to be within the scope of the disclosure.

What is claimed is:

1. A surgical device, comprising:
   a tool assembly having an anvil assembly and a cartridge assembly configured to grasp tissue therebetween, the cartridge assembly including a plurality of surgical fasteners;
   a motor configured to fire one or more surgical fasteners;
   a sensor configured to determine a first parameter of the tool assembly; and
   a control system configured to predict a speed at which the one or more surgical fasteners are to be fired based on the first parameter detected by the sensor.

2. The surgical device of claim 1, wherein the first parameter is a clamp force between the anvil assembly and the cartridge assembly.

3. The surgical device of claim 2, wherein the control system is configured to control the motor to fire the one or more staples at the predicted speed based on the clamp force.

4. The surgical device of claim 2, wherein the control system is configured to adjust a wait time between a clamping state of the surgical device and a staple firing state of the surgical device based on the clamp force.

5. The surgical device of claim 1, wherein the sensor is a strain gauge.

6. The surgical device of claim 1, further comprising a display configured to display the predicted speed at which the one or more surgical fasteners are to be fired.

7. A method of stapling tissue with a surgical device having a tool assembly with a cartridge assembly and an anvil assembly and a motor configured to actuate the tool assembly, the method comprising:
   determining a clamp force between the cartridge assembly and the anvil assembly;
   predicting a speed at which one or more surgical fasteners are to be fired by the motor of the surgical device based on the clamp force.

8. The method of claim 7, further comprising displaying the predicted speed at which the one or more surgical fasteners are to be fired by the motor of the surgical device.

* * * * *